US012569472B2

(12) United States Patent
Agrawal

(10) Patent No.: US 12,569,472 B2
(45) Date of Patent: Mar. 10, 2026

(54) PPARγ AGONISTS FOR TREATMENT OF KIDNEY DISEASE

(71) Applicant: The Research Institute at Nationwide Children's Hospital, Columbus, OH (US)

(72) Inventor: Shipra Agrawal, Upper Arlington, OH (US)

(73) Assignee: THE RESEARCH INSTITUTE AT NATIONWIDE CHILDREN'S HOSPITAL, Columbus, OH (US)

(*) Notice: Subject to any disclaimer, the term of this patent is extended or adjusted under 35 U.S.C. 154(b) by 693 days.

(21) Appl. No.: 17/920,556

(22) PCT Filed: Apr. 27, 2021

(86) PCT No.: PCT/US2021/029376

§ 371 (c)(1),
(2) Date: Oct. 21, 2022

(87) PCT Pub. No.: WO2021/222231

PCT Pub. Date: Nov. 4, 2021

(65) Prior Publication Data

US 2023/0201169 A1 Jun. 29, 2023

Related U.S. Application Data

(60) Provisional application No. 63/016,039, filed on Apr. 27, 2020.

(51) Int. Cl.

| | |
|---|---|
| ***A61K 31/426*** | (2006.01) |
| ***A61K 45/06*** | (2006.01) |
| ***A61P 13/12*** | (2006.01) |

(52) U.S. Cl.

CPC ............ *A61K 31/426* (2013.01); *A61K 45/06* (2013.01); *A61P 13/12* (2018.01)

(58) Field of Classification Search

CPC .............................. A61K 31/426; A61P 13/12

See application file for complete search history.

(56) References Cited

U.S. PATENT DOCUMENTS

| | | | | |
|---|---|---|---|---|
| 10,034,868 | B2 * | 7/2018 | Tharaux .................. | A61P 13/12 |
| 10,927,069 | B2 | 2/2021 | Imig et al. | |
| 2018/0015090 | A1 | 1/2018 | Lin et al. | |
| 2020/0069745 | A1 | 3/2020 | Wu et al. | |
| 2020/0215072 | A1 | 7/2020 | Symonds et al. | |
| 2020/0331868 | A1 | 10/2020 | Zhang et al. | |
| 2021/0059997 | A1 | 3/2021 | Oki et al. | |

FOREIGN PATENT DOCUMENTS

| | | | |
|---|---|---|---|
| WO | 2004/089276 | A2 | 10/2004 |
| WO | 2019/141229 | A1 | 7/2019 |
| WO | 2019/236844 | A1 | 12/2019 |
| WO | A2019131897 | A1 | 12/2020 |

OTHER PUBLICATIONS

Amato et al., "GQ-16, a Novel Peroxisome Proliferator-activated Receptor γ (PPARγ) Ligand, Promotes Insulin Sensitization without Weight Gain", The Journal of Biological Chemistry, vol. 287, No. 33, pp. 28169-28179 (Aug. 2012).*

Imig, J. D., et al.; "Soluble epoxide hydrolase inhibition and peroxisome proliferator activated receptor agonist improve vascular function and decrease renal injury in hypertensive obese rats"; Experimental Biology and Medicine, vol. 237 No. 12; Dec. 1, 2012; pp. 1402-1412. doi:10.1258/ebm.2012.012225.

Srinivasa R. Vulichi, et al.; "Concise perspectives on some synthetic thiazolidine-2,4-dione derivatives and their specific pharmacodynamic aspects"; Life Sciences vol. 271, Apr. 1, 2021; p. 119182, XP093145647; doi: 10.1016/j.lfs.2021.119182.

Applicant: The Research Institute at nationwide Children's Hospital; "PPARy Agonists for Treatment of Kidney Disease"; European Application No. 21797007.8; Extended European Search Report dated Apr. 22, 2024; 10 pgs.

* cited by examiner

*Primary Examiner* — Kevin E Weddington

(74) *Attorney, Agent, or Firm* — Tarolli, Sundheim, Covell & Tummino LLP

(57) ABSTRACT

A method of treating or preventing glomerular disease or chronic kidney disease in a subject is described. The method includes administering to the subject a therapeutically effective amount of PPARγ agonist or a pharmaceutically acceptable salt thereof.

11 Claims, 8 Drawing Sheets

A
NPHS1 / RPL6 (mRNA FOLD CHANGE)
CONTROL
PAN
PAN + PIO
PAN + GQ-16

B
NPHS1
UPCr (mg/mg)

C
NRL2 / RPL6 (mRNA FOLD CHANGE)

D
NLR2

E
TRPC6 (mRNA FOLD CHANGE)

F
TRPC6

G
NPHS1 / RPL6 (mRNA FOLD CHANGE)
NS
P=0.06

H
PPARG

I
SET 1
SET 2
SET 3
P-PPARγ(SER273)
PPARγ
GAPDH

J
P-PPARγ/ TOTAL PPAR
PAN + GQ

K

PPARγ AGONISTS FOR TREATMENT OF KIDNEY DISEASE

CROSS-REFERENCE TO RELATED APPLICATIONS

This application was a national stage application claiming the benefit of International Patent Application No. PCT/US2021/029376, filed on Apr. 27, 2021, which claimed the benefit of U.S. Provisional Application No. 63/160,039, filed Apr. 27, 2020, both of which are incorporated herein by reference in their entirety.

BACKGROUND

Various forms of glomerular disease, manifesting as nephrotic syndrome (NS) with high-grade proteinuria, can be frequently refractory to treatment leading to progression to chronic kidney disease and end-stage kidney disease (ESKD). Additionally, NS is typically associated with edema, hypoalbuminemia, dyslipidemia, systemic immune dysregulation, and hypercoagulopathy. In order to identify effective treatments for glomerular disease, we and others have previously reported that peroxisome proliferator-activated receptor γ(PPARγ) agonists and thiazolidinediones (TZDs) such as pioglitazone (Pio), directly protect podocytes from injury (Kanjanabuch et al., Kidney Int, 71: 1232-1239 (2007)) and reduce proteinuria and glomerular injury in various animal models of glomerular disease. Yang et al., Journal of the American Society of Nephrology: JASN, 20: 2380-2388 (2009). They have also been shown to improve clinical outcomes in NS patients refractory to steroid treatment. Agrawal et al., Sci Rep, 6: 24392 (2016). Moreover, these protective effects in experimental models have been shown to be mediated by activation of podocyte PPARγ, thus indicating a pivotal role for PPARγ in maintaining glomerular function through the preservation of podocytes even in non-diabetic glomerular diseases in addition to their general beneficial metabolic, insulin-sensitizing and anti-inflammatory effects. Agrawal et al., Nat Rev Nephrol, 17(3):185-204 (2021).

Since the identification of PPARs in 1990, PPARγ has been recognized as a nuclear receptor superfamily member, a ligand-dependent transcription factor, and a master regulator of adipogenesis and metabolism. The ability of PPARγ to regulate adipogenesis and lipid storage accounts for the insulin sensitizing effects of its agonists or anti-diabetic drugs known as TZDs. Heikkinen et al., Biochimica et biophysica acta, 1771: 999-1013 (2007). Interestingly, in patients with diabetic nephropathy (DN), TZDs have been shown to exhibit antiproteinuric effects in a meta-analyses study as well as a decrease in urinary podocyte loss. Nakamura et al., Metabolism, 50: 1193-1196 (2001). Moreover, PPARγ can exist in tissue-specific and function-specific forms which can be generated due to alternative splicing and promoter usage (Fajas et al., The Journal of biological chemistry, 272: 18779-18789 (1997)) as well as its differential phosphorylation, specifically at Serine (Ser) 273 (Choi et al., Nature, 477: 477-481 (2011)), which have been shown to be important determinants of its effects on adipogenesis and insulin sensitivity (FIG. 1). However, the roles of PPARγ alternative splicing or differential phosphorylation in glomerular disease are unexplored.

Targeting PPARγ via two widely marketed anti-diabetic drugs, the TZDs Pio and especially rosiglitazone, has been under recent scrutiny because of reported side effects such as weight gain, increased risk of edema, heart failure, bone loss, and bladder cancer. Yki-Jarvinen, H., The New England journal of medicine, 351: 1106-1118 (2004). More recently, breakthrough discoveries in the field of PPARγ biology has led to the generation of a series of novel compounds with a weak traditional PPARγ agonistic activity (adipogenic), but very good antidiabetic activity 30. Choi et al., Nature, 466: 451-456 (2010). GQ-16, a novel PPARγ partial agonist has been demonstrated to block receptor phosphorylation at Ser273 in an in vitro assay and has been shown to improve insulin sensitivity in diabetic mice in the absence of weight gain and edema. Amato et al., The Journal of biological chemistry, 287: 28169-28179 (2012). Moreover, GQ-16 treatment is accompanied by induction of thermogenesis-related genes in epididymal fat depots, suggesting that browning of visceral WAT may have contributed to weight loss. Coelho et al., PloS one, 11: e0154310 (2016). This advantageous pharmacological profile appears to be due to the unique binding mode of GQ-16 to PPARγ and stabilization of beta sheets, which is distinct from traditional TZDs. Targeting PPARγ may therefore have additional therapeutic potential.

SUMMARY OF THE INVENTION

The inventors hypothesized that PPARγ agonists exhibiting a distinct binding mode from other reported PPARγ ligands could be used for the treatment of glomerular disease or chronic kidney diseases in which PPARγ plays a role, while exhibiting fewer side effects than existing therapeutic agents for treatment of chronic kidney disease.

Accordingly, in one aspect, a method of treating or preventing glomerular disease or chronic kidney disease in a subject is provided. The method includes administering to the subject a therapeutically effective amount of PPARγ agonist. In some embodiments, the agonist is a partial agonist, in some embodiments the agonist is a GQ-16 derivative, while in other embodiments the agonist is selected from GQ-16, MRL-24, and PA-082, or a pharmaceutically acceptable salt thereof. In some embodiments, the PPARγ agonist is administered together with a pharmaceutically acceptable carrier.

In some embodiments, the method treats or prevents chronic kidney disease. In some embodiments, the glomerular disease is nephrotic syndrome. In further embodiments, the treatment decreases proteinuria in the subject. In yet further embodiments, the treatment decreases hypercoagulopathy in the subject.

In some embodiments, the method is used to prevent glomerular disease or chronic kidney disease in a subject in need thereof. In additional embodiments, the method is used to treat chronic kidney disease in a subject having been diagnosed with chronic kidney disease. In yet further embodiments, the method includes administering an additional therapeutic agent for treating or preventing kidney disease.

BRIEF DESCRIPTION OF THE FIGURES

The present invention may be more readily understood by reference to the following drawings, wherein.

Figure 1:
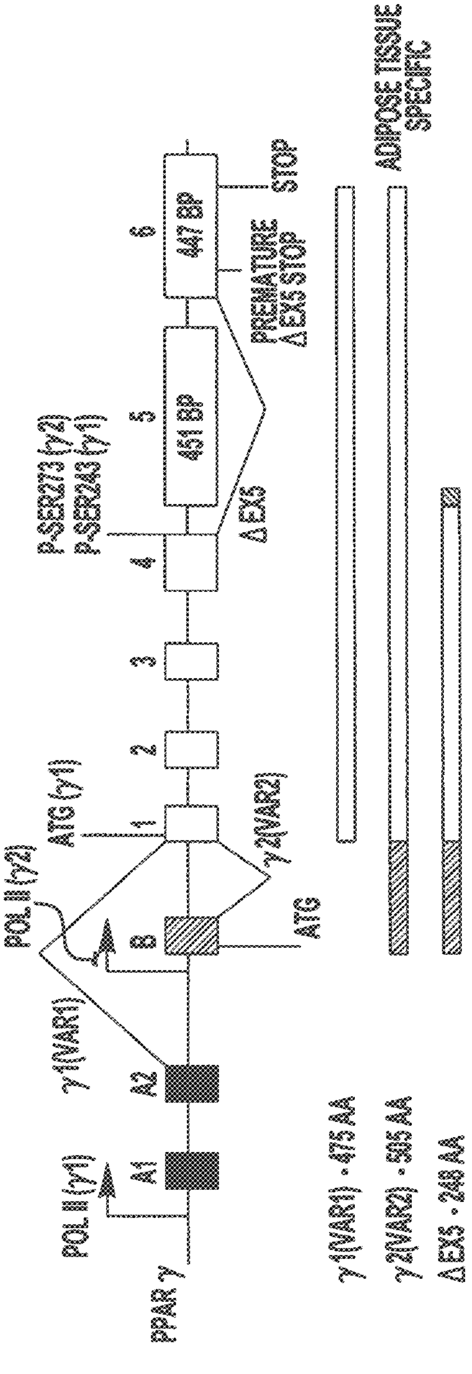
FIG. 1 provides a schematic representation showing the PPARγ isoforms and phosphorylation site. PPARγ exists in mainly two major isoforms, γ1 and γ2, which are a result of different promoter usage by RNA Polymerase II (depicted in tall arrows) as well as alternative splicing (depicted by exon skipping), resulting in variants 1 and 2. While, γ1 variant 1 includes exons A1 and A2 upstream of the start codon (ATG)

on exon 1, γ2 variant 2 contains the transcription start site preceding exon B and initiates translation on the start codon (ATG) in exon B, resulting in γ2 protein product, which is 30 amino acids longer than γ1. In a relatively unexplored variant that skips exon 5 (Δex5), a frameshift occurs on exon 6 due to exon 5 being spliced out, which creates a premature stop codon. One of the major sites of phosphorylation on Serine 273 (Ser273) is depicted. This is coded by the last codon on exon 4, thus it remains conserved in variant1, variant 2, and Δex5. The relative position of Ser273 is changed to Ser243 in the isoform γ2. This figure depicts the human annotations for variants 1 (var1: NM_138712) and 2 (var2: NM_015869) encoding isoforms γ1 and γ2. These variants and isoforms correspond to reversed numbers in rat and are annotated as 2 (var2: NM_001145366) and 1 (var1: NM_013124), respectively.

FIGS. 2A-2D provide graphs and images showing GQ-16 reduces proteinuria and hypoalbuminemia with increased efficacy compared to Pio in a rat model of PAN-induced nephropathy. Proteinuria was induced in male Wistar rats after single intravenous injection of PAN (50 mg/kg) on Day 0. Treatment groups received pioglitazone (Pio, 10 mg/kg; n=7) or GQ-16 (40 mg/kg; n=7) daily by oral gavage for 11 days. (A) Urinary protein/creatinine ratios (UPCr) were plotted from Day 11 urine samples (*p<0.05, p<0.01, *p<0.001, ns=p>0.05; as determined by Mann-Whitney test). (B) Representative gels of induced proteinuria after PAN injections and treatments with Pio and GQ-16. Equal volumes (5 μl) of urine from selected days were analyzed by SDS-polyacrylamide gel electrophoresis and Coomassie Blue staining. (C) Serum albumin concentrations from Day 11 were plotted for the four groups (*p<0.05, ns=p>0.05, as determined by Mann-Whitney test). (D) Linear regression was performed on all the rats combined which showed correlation of serum albumin with proteinuria.

FIGS. 3A-3K provide graphs and images showing glomerular gene expression of podocyte marker Nphs1 and PPARγ target gene Nrf2 is restored with treatment. Glomerular gene expression was measured by real time RT-PCR from total RNA extracted from the glomeruli isolated from Control, PAN-injected, and PAN-injected rats treated with Pio or GQ-16 ((n≥3/group, assay in triplicates). Mean±SEM plotted of (A) Nphs1, (C) Nrf2, (E) Trpc6, and (G) Pparg (*p<0.05, p<0.01, *p<0.001, ****p<0.0001 as determined by Student t-test). Nphs1, Nrf2, and Pparg expression was normalized to house-keeping gene Rp16. Linear regression analyses were performed to correlate proteinuria with (B) Nphs1, (D) Nrf2, (F) Trpc6, and (H) Pparg. Total protein was isolated from Control, PAN-injected, and PAN-injected rats treated with Pio and GQ-16 from glomeruli; (I) western blot was performed on the samples for P-PPARγ (Ser273) and total PPARγ, (J) P-PPARγ/total PPARγ density plotted, and (K) linear regression analysis performed with UPCr.

FIGS. 4A-4D provide graphs showing glomerular disease associated hypercoagulopathy is corrected with GQ-16 treatment. Endogenous thrombin potential (ETP) was measured using a thrombin generation assay (TGA) on plasma from rats in each group of PAN-injured, and Pio and GQ-16 treated rats (n=4-7/group). (A) Typical thrombin generation curve with ETP, peak height, velocity index, and lag time are labeled. (B) Representative graphs of thrombin generation from one rat from each group. (C) Mean±SEM of ETP plotted with the individual values shown. (D) Linear regression analysis to correlate proteinuria with ETP. *p<0.05 as determined by Student t-test.

FIGS. 5A-5D provide graphs showing GQ-16 treatment reduces glomerular disease-associated hypercholesterolemia and alters hepatic gene expression. Serum cholesterol concentration was measured from Day 11 serum samples and (A) plotted as Mean±SEM. (B) Linear regression correlating serum cholesterol with proteinuria. Hepatic gene expression was measured by real time RT-PCR from total RNA extracted from liver tissue from Control, PAN-injected, and PAN-injected rats treated with Pio and GQ-16 (n≥3/group, assay in triplicates). (C) Pcsk9 and (D) Abca1 gene expression was normalized to liver housekeeping gene Ppia. Mean±SEM plotted; *p<0.05, **p<0.01 as determine by unpaired Student t-test.

FIGS. 6A-6D provide graphs showing GQ-16 and Pio treatments distinctly alter the gene expression of adipogenic pathways in the white adipose tissue. White adipose tissue gene expression was measured by real time RT-PCR from total RNA extracted from epididymal fat tissue from Control, PAN-injected, and PAN-injected rats treated with Pio and GQ-16 (n≥3/group, assay in triplicates). Expression of mRNA from (A) Ap2, (B) Adipoq, (C) Adipsin, and (D) Cd36 was determined and normalized to the fat housekeeping gene Ppia. Mean±SEM plotted and *p<0.05, p<0.01, *p<0.001, ****p<0.0001 as determined by Student t-test.

Figure 7A:
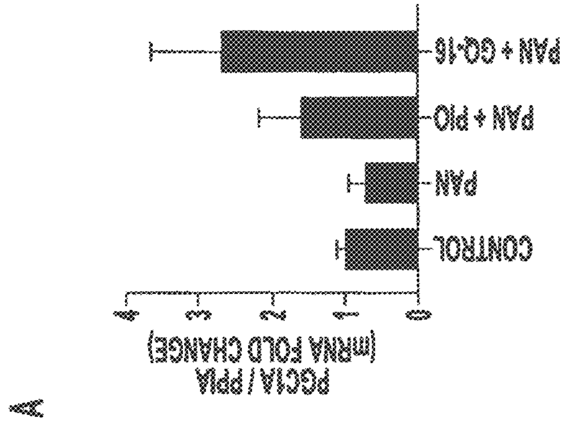
Figure 7B:
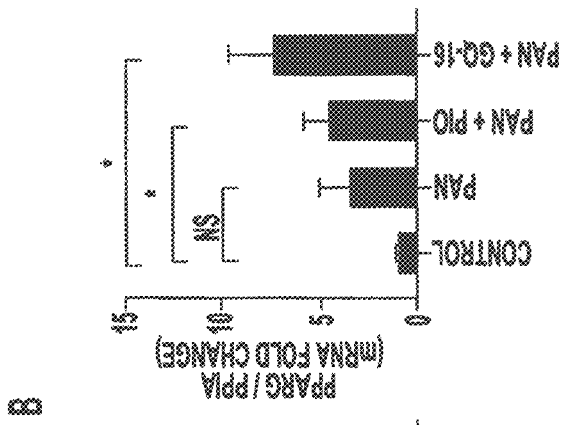
Figure 7C:
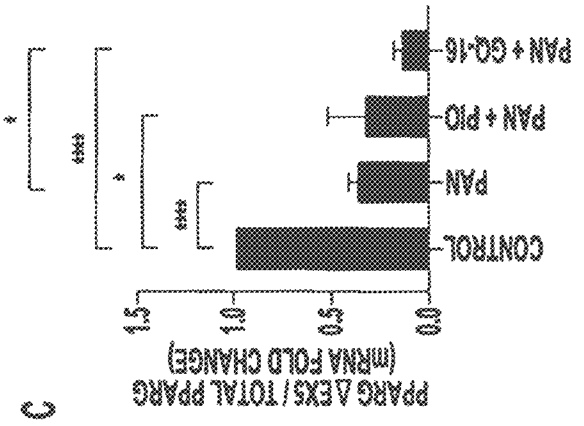

FIGS. 7A-7C provide graphs showing GQ-16 treatment induces Pparg expression and reduces Δ exon-5 splice variant form. White adipose tissue gene expression was measured by real time RT-PCR from total RNA extracted from epididymal fat tissue from Control, PAN-injected, and PAN-injected rats treated with Pio and GQ-16 (n≥3/group, assay in triplicates). Expression of mRNA from (A) Pgc1a, and (B) Pparg was determined and normalized to the fat house-keeping gene Ppia. (C) Expression of Pparg Δ exon 5 splice variant form was measured and normalized to Pparg. Mean±SEM plotted and *p<0.05, p<0.01, *p<0.001, ****p<0.0001 as determined by Student t-test.

Figure 8:
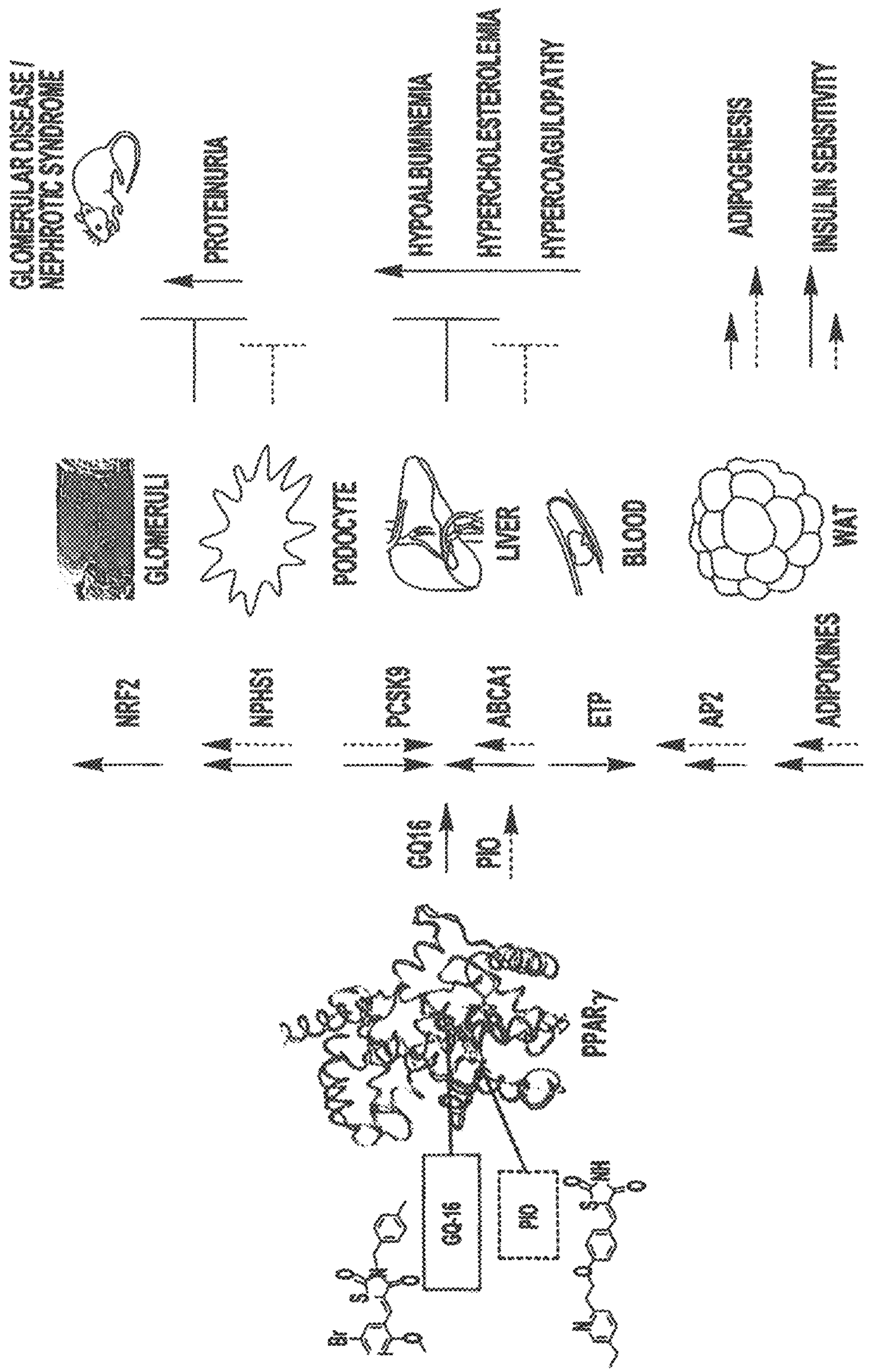

FIG. 8 provides a schematic representation depicting the superiors effects of GQ-16 in improving glomerular disease. The traditional full agonist of PPARγ, pioglitazone (Pio) and the partial agonist, GQ-16, both bind and activate PPARγ, although in distinct ways. GQ-16 provides a better efficacy in reducing proteinuria and in reducing overall nephrotic syndrome-associated features such as hypoalbuminemia, hypercholesterolemia and hypercoagulopathy, than Pio. These effects are associated with increased glomerular Nrf2 expression, increased expression of Nphs1 in podocytes, decreased hepatic expression of Pcsk9 and increased hepatic Abca1 expression, and reduced endogenous thrombin potential (ETP) in the plasma of nephrotic rats treated with GQ-16. Moreover, GQ-16 increases white adipose tissue (WAT) aP2 to a lesser extent than Pio and increases the expression of adipokines to a larger extent than Pio, which likely render reduced adipogenesis and increased insulin sensitivity as compared to Pio. Solid arrows and lines represent GQ-16 effects and dashed arrows and lines represent the effects of Pio.

DETAILED DESCRIPTION OF THE INVENTION

The present invention provides a method of treating or preventing glomerular disease or chronic kidney disease in a subject. The method includes administering to the subject a therapeutically effective amount of PPARγ agonist or a pharmaceutically acceptable salt thereof.

Definitions

The terminology as set forth herein is for description of the embodiments only and should not be construed as limiting of the invention as a whole. As used in the description of the invention and the appended claims, the singular forms "a", "an", and "the" are inclusive of their plural forms, unless contraindicated by the context surrounding such.

Treat", "treating", and "treatment", etc., as used herein, refer to any action providing a benefit to a subject at risk for or afflicted with a condition or disease such as chronic kidney disease, including improvement in the condition through lessening or suppression of the major symptom of proteinuria such as proteinuria and/or lessening of associated complications such as hypercoagulopathy, delay in progression of the disease, etc. The subject may be at risk due to the presence of a risk factor such as heart failure, hepatitis, diabetes, being genetically predisposed to chronic kidney disease, and so on.

The term "in need of treatment" as used herein refers to a judgment made by a caregiver that a patient requires or will benefit from treatment. This judgment is made based on a variety of factors that are in the realm of a caregiver's expertise, but that includes the knowledge that the patient is ill, or will be ill, as the result of a disease or condition that is treatable by a method or compound of the disclosure.

Prevention, as used herein, refers to any action providing a benefit to a subject at risk of being afflicted with a condition or disease such as chronic kidney disease, including avoidance of the development of glomerular or chronic kidney disease or a decrease of one or more symptoms of the disease should chronic kidney disease develop.

Within the present invention, a "therapeutically effective amount" of a composition is that amount which is sufficient to show a benefit (e.g., a reduction in a symptom associated with the disorder, disease, or condition being treated) while avoiding adverse side effects such as those typically associated with alternative therapies. The therapeutically effective amount may be administered in one or more doses.

As used herein, the term "pharmaceutically acceptable carrier" refers to carriers that do not negatively affect the biological activity of the therapeutic molecule or compound to be placed therein. The characteristics of the delivery vehicle will depend on the route of administration. Therapeutic compositions may contain, in addition to the active compound, diluents, fillers, salts, buffers, stabilizers, solubilizers, and other materials well known in the art. A pharmaceutically acceptable carrier can deliver the active agent without unduly deleterious side effects in light of the severity of the disease and necessity of the treatment.

A subject, as defined herein, is an animal, preferably a mammal such as a domesticated farm animal (e.g., cow, horse, pig) or a pet (e.g., dog, cat). More preferably, the subject is a human. The subject may also be a subject in need of treatment of a chronic kidney disease or glomerular disease.

As used herein, the term "organic group" is used for the purpose of this invention to mean a hydrocarbon group that is classified as an aliphatic group, cyclic group, or combination of aliphatic and cyclic groups (e.g., alkaryl and aralkyl groups). In the context of the present invention, suitable organic groups for GQ-16 derivatives are those that do not interfere with the compound's ability to act as a PPARγ agonist. In the context of the present invention, the term "aliphatic group" means a saturated or unsaturated linear or branched hydrocarbon group. This term is used to encompass alkyl, alkenyl, and alkynyl groups, for example.

As used herein, the terms "alkyl", "alkenyl", and the prefix "alk-" are inclusive of straight chain groups and branched chain groups and cyclic groups, e.g., cycloalkyl and cycloalkenyl. Unless otherwise specified, these groups contain from 1 to 20 carbon atoms, with alkenyl groups containing from 2 to 20 carbon atoms. In some embodiments, these groups have a total of at most 10 carbon atoms, at most 8 carbon atoms, at most 6 carbon atoms, or at most 4 carbon atoms. Lower alkyl groups are those including at most 6 carbon atoms. Examples of alkyl groups include haloalkyl groups and hydroxyalkyl groups.

The term "haloalkyl" is inclusive of groups that are substituted by one or more halogen atoms, including perfluorinated groups. This is also true of other groups that include the prefix "halo-". Examples of suitable haloalkyl groups are chloromethyl, trifluoromethyl, and the like. A halo moiety can be chlorine, bromine, fluorine, or iodine.

Cycloalkyl groups are cyclic alkyl groups containing 3, 4, 5, 6, 7 or 8 ring carbon atoms like cyclopropyl, cyclobutyl, cyclopentyl, cyclohexyl or cyclooctyl, which can also be substituted and/or contain 1 or 2 double bounds (unsaturated cycloalkyl groups) like, for example, cyclopentenyl or cyclohexenyl can be bonded via any carbon atom.

A heterocyclyl group means a mono- or bicyclic ring system in which one or more carbon atoms can be replaced by one or more heteroatoms such as, for example, 1, 2 or 3 nitrogen atoms, 1 or 2 oxygen atoms, 1 or 2 sulfur atoms or combinations of different hetero atoms. The heterocyclyl residues can be bound at any positions, for example on the 1-position, 2-position, 3-position, 4-position, 5-position, 6-position, 7-position or 8-position.

The term "aryl" as used herein includes carbocyclic aromatic rings or ring systems. Examples of aryl groups include phenyl, naphthyl, biphenyl, anthracenyl, phenanthracenyl, fluorenyl and indenyl. Aryl groups may be substituted or unsubstituted.

In one aspect, the present invention provides a method of treating chronic kidney disease in a subject. The method includes administering to the subject a therapeutically effective amount of PPARγ agonist, or a pharmaceutically acceptable salt thereof. The PPARγ agonist can be PPARγ agonist that strongly stabilizes the β-sheet region of the PPARγ receptor, thus inhibiting Ser-273 phosphorylation by the Cdk5 kinase. See Desai et al., Expert Opin Ther Pat., 25(4):479-88 (2015). In some embodiments, the PPARγ agonist is a partial PPARγ agonist.

Peroxisome Proliferator-Activated Receptor γ Agonists

The method of the invention includes administering a PPARγ agonist to a subject. In some embodiments, the subject is one who has been identified as being in need of treatment. A PPARγ agonist is a chemical that binds to a PPARγ receptor and activates the receptor. Takada I & Makishima M., Expert Opin Ther Pat., 30(1):1-13 (2020). Many thiazolidinedione compounds specifically bind to and activate PPARγ receptors, and are PPARγ agonists. Agonists include full agonists, which bind to and activate a receptor with the maximum response that an agonist can elicit at the receptor, and partial agonists, which bind to and activate a specific receptor, but have only partial efficacy at the receptor relative to a full agonist. The affinity of an agonist for its receptor is measured by its $K_i$ (i.e., affinity constant) value. Preferably, the PPARγ agonist used in the method of the invention has a $K_i$ having a value ranging from 50 nM to 500 nM. For example, the $K_i$ of GQ-16 is 160 nM.

Partial PPARγ agonists are PPARγ ligands with insulin-sensitizing activity and lower stimulation of adipogenesis. Because partial PPARγ agonists bind to the ligand-binding pocket of the PPARγ receptor in distinct manners, binding by these ligands induces the displacement of the differential cofactor and the specific gene expression in a tissue-specific manner.

The PPARs nuclear receptors mainly consist of three subtypes (PPARα, PPARγ, and PPARδ/β). All three PPAR isoforms possess similar structural and functional features. PPARγ is expressed in adipose tissue, promoting adipogenesis and increasing lipid storage. PPARγ has at least two promoters, and results in the production of two isoforms, 1 and 2. These isoforms are expressed in a tissue-specific pattern. The PPARγ1 isoform is expressed in the spleen, intestine, kidney, and white adipose tissue, while the PPARγ2 is preferentially expressed in white and brown fat. PPARγ2 is most abundantly expressed in fat cells, and plays a pivotal role in fat cell differentiation and lipid storage.

Examples of suitable PPARγ agonists include GQ-16 and its derivatives. GQ-16 (5-(5-bromo-2-methoxy-benzylidine)-3-(4-methyl-benzyl)-thiazolidine-2,4-dione) can be synthesized using the method described by da Costa Leite (Eur. J. Med. Chem. 42, 1263-1271 (2007)), and has the structure shown below:

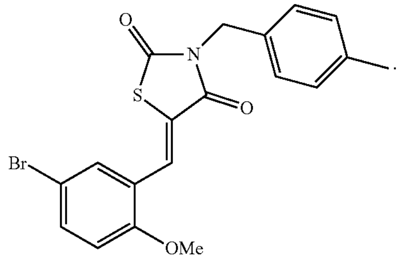 [SMILES: COc1ccc(Br)cc1/C=C1\SC(=O)N(Cc2ccc(C)cc2)C1=O]

Although GQ-16 has an overall structure similar to that of rosiglitazone, GQ-16 binds to PPARγ in a different orientation than traditional TZDs, such as rosiglitazone. GQ-16 makes no direct contacts with residues of helix 12 of PPARγ, a hallmark of traditional TZDs. Rather, GQ-16 binds to Ser-273 of the Cdk5 recognition site.

GQ-16 derivatives include compounds having the benzylidine thiazolidine-2,4-dione backbone, with various side chain groups that do not interfere with the ability of the derivative to function as a PPARγ agonist, which can readily be identified using an assay for PPARγ affinity or agonist activity, or by determining their ability to bind to Ser-273 of the Cdk5 recognition site. Examples of GQ-16 derivatives include GQ-19 (3-(4-Methyl-benzyl)-5-(4-nitro-benzylidene)-thiazolidine-2,4-dione); GQ-21 (5-(3-Bromo-benzylidene)-3-(4-methyl-benzyl)-thiazolidine-2,4-dione), GQ-22 (5-(3-Bromo-4-methoxy-benzylidene)-3-(4-methyl-benzyl)-thiazolidine-2,4-dione), GQ-88 (5-(5-Bromo-2-methoxy-benzylidene)-3-(2-chloro-6-fluoro-benzyl)-thiazolidine-2,4-dione), GQ-177 (3-(3-Bromo-benzyl)-5-(4-methanesulfonyl-benzylidene)-thiazolidine-2,4-dione), GQ-288 (5-(2-chloro-5-nitrobenzylidene)-3-(4-methylbenzyl)thiazolidine-2,4-dione), GQ-289 (5-(3-methoxybenzylidene)-3-(4-methylbenzyl)thiazolidine-2,4-dione), GQ-398 (3-(3-methoxybenzyl)-5-(4-nitrobenzylidene)thiazolidine-2,4-dione), GQ-402 (5-(5-bromo-2-methoxybenzylidene)-3-(3-methoxybenzyl)thiazolidine-2,4-dione), GQ-410 (3-(3-methoxybenzyl)-5-(4-methylbenzylidene)thiazolidine-2,4-dione), and GQ-417 (3-(3-methoxybenzyl)-5-(3-nitrobenzylidene)thiazolidine-2,4-dione).

In some embodiments, the PPARγ agonist is selected from the group of compounds including GQ-16, MRL-24, and PA-082. In some embodiments, the PPARγ agonist is GQ-16. GQ-16, In some embodiments, the PPARγ agonist is MRL-24. MRL-24 ((S)-2-(3-((1-(4-Methoxybenzoyl)-2-methyl-5-(trifluoromethoxy)-1H-indol-3-yl)methyl)phenoxy)propanoic acid) has the structure shown below:

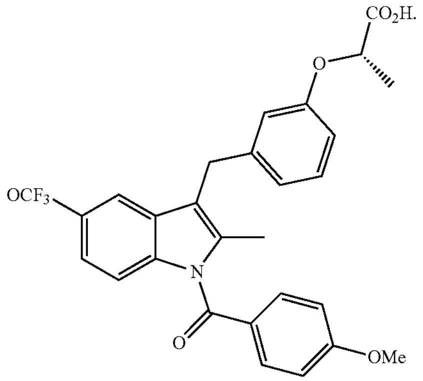 [SMILES: COc1ccc(C(=O)n2c(C)c(Cc3cccc(O[C@@H](C)C(=O)O)c3)c3cc(OC(F)(F)F)ccc32)cc1]

In some embodiments, the PPARγ agonist is PA-082. PA-082, an isoquinoline derivative (see Burgermeister, E., Schnoebelen, A, Molecular Endocrinology, vol. 20, no. 4, pp. 809-830 (2006)), has the structure shown below:

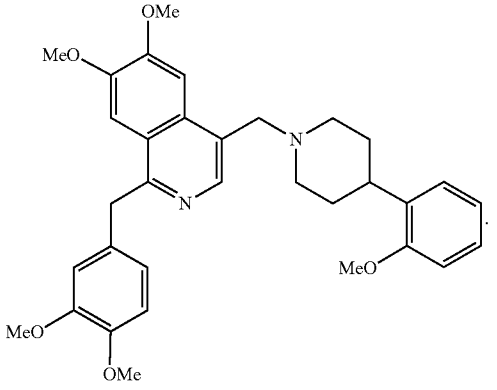 [SMILES: COc1ccc(Cc2ncc(CN3CCC(c4ccccc4OC)CC3)c3cc(OC)c(OC)cc23)cc1OC]

Chronic Kidney Disease

The method includes treating or preventing chronic kidney disease in a subject. Chronic kidney disease is a type of kidney disease in which there is gradual loss of kidney function over a period of months to years. Chronic kidney disease can be caused by a variety of different factors, with the most common being diabetes mellitus, hypertension, and glomerulonephritis. Symptoms of chronic kidney disease include increased blood pressure, accumulation of urea, hyperkalemia, edema, hyperphosphatemia, hypocalcemia, metabolic acidosis, and anemia. Types of chronic kidney disease include vascular kidney disease (e.g., kidney artery stenosis), glomerular disease, tubulointerstitial disease (e.g., toxin-induced tubulointerstitial nephritis), and obstructive nephropathy. Chronic kidney disease can be diagnosed by measurement of serum creatinine levels, examination of the patient, and/or the use of a urine dipstick. Signs of chronic kidney disease and the resulting kidney damage are seen in blood, urine, or imaging studies which includes lab albumin/creatinine ratio (ACR)≥30. All people with a glomular filtration rate <60 ml/min/1.73 $m^2$ for 3 months are defined as having chronic kidney disease.

Treatment of chronic kidney disease can include reduction of a variety of symptoms associated with chronic kidney disease. In some embodiments, treatment decreases proteinuria in the subject. Proteinuria is a disorder in which an excess amount of protein is found in the urine. Proteinuria is defined as urine having a protein/creatinine ratio greater than 45 mg/mmol. In other embodiments, treatment decreases hypercoagulopathy in the subject. Hypercoagulopathy, also known as thrombophilia, is an abnormality of blood coagulation that increases the risk of thrombosis. Hypercoagulopathy can be determined by measuring one or more blood coagulation factors such as blood count, thrombin time, or prothrombin time.

In some embodiments, the method is used to prevent glomerular disease or chronic kidney disease in a subject in need thereof. Prevention refers to preventing the disease or a symptom of a disease from occurring in a subject. A subject who is in need of prevention is one who has been identified as being predisposed to the disease but has not yet been diagnosed as having it (e.g., including diseases that may be associated with or caused by a primary disease). Prevention may include completely or partially preventing a disease or symptom. In some embodiments, prevention also includes reducing the risk that a subject will develop the disease, while not guaranteeing that the disease will be prevented. For example, prevention can reduce the likelihood that a subject will develop the disease or one or more symptoms of the disease by 10%, 20%, 30%, 40%, 50%, 60%, 70%, 80%, 90%, or 100% compared with a subject who has not been administered a PPARγ agonist to prevent occurrence of glomerular disease or chronic kidney disease.

In some embodiments, the method can be used to treat or prevent glomerular disease. Glomerular diseases affect the function of the kidneys and the glomeruli, which are small units within the kidney where blood is cleaned. Glomerular diseases include many conditions with a variety of genetic and environmental causes, but they fall into two major categories: Glomerulonephritis, which describes the inflammation of the membrane tissue in the kidney that serves as a filter, separating wastes and extra fluid from the blood, and glomerulosclerosis, which describes the scarring or hardening of the tiny blood vessels within the kidney. In some cases, glomerular disease results in chronic kidney disease, though this is not always the case. Although glomerulonephritis and glomerulosclerosis have different causes, they can both lead to kidney failure. Examples of glomerular disease include nephrotic syndrome, minimal change disease, diabetic nephropathy, and other conditions known to those skilled in the art.

Glomerular diseases damage the glomeruli, letting protein and sometimes red blood cells leak into the urine. Glomerular disease can also interfere with the clearance of waste products by the kidney, so they begin to build up in the blood. Furthermore, loss of blood proteins like albumin in the urine can result in a fall in their level in the bloodstream. When albumin leaks into the urine, the blood loses its capacity to absorb extra fluid from the body. Fluid can accumulate outside the circulatory system in the face, hands, feet, or ankles and cause swelling. Symptoms of glomerular disease include albuminuria, hematuria, reduced glomerular filtration rate, proteinuria, and edema.

In some embodiments, the glomerular disease is nephrotic syndrome. Nephrotic syndrome (NS) is a general term that refers to the loss of protein in the urine (proteinuria), hyperlipidemia (hypercholesterolemia and hypertriglyceridemia), dyslipidemia, and edema. Nephrotic syndrome involves changes in the pathology of cells in the kidney, such as podocytes. Many conditions are categorized as nephrotic syndromes, including minimal change disease (MCD), focal segmental glomerulosclerosis (FSGS), membranous nephropathy (MN) (also called membranous glomerulonephritis, MGN), and membranoproliferative glomerulonephritis (MPGN). For years pathologists found no changes in MCD tissue when viewing specimens under light microscopy, hence the name minimal change disease. With the advent of electron microscopy, the changes now known as the hallmarks for the disease include diffuse loss of podocyte foot processes, vacuolation of the podocyte foot processes, and growth of microvilli on the visceral epithelial cells. Diabetic nephropathy is the most common cause of nephrotic syndrome.

A variety of signs and symptoms are known to be associated with nephrotic syndrome. These include respiratory tract infection, allergy, macrohematuria, symptoms of infection, hypotension, respiratory distress, tachypnea, seizure, anorexia, irritability, fatigue, and disarrhea. Nephrotic syndrome can be diagnosed using urinalysis, urine protein quantification, serum albumin quantification, and a lipid panel. With the advent of electron microscopy, the changes now known as the hallmarks for the disease include diffuse loss of podocyte foot processes, vacuolation of the podocyte foot processes, and growth of microvilli on the visceral epithelial cells. Diabetic nephropathy is the most common cause of nephrotic syndrome.

Nephrotic syndrome, or nephrosis, is defined by the presence of nephrotic-range proteinuria, edema, hyperlipidemia, and hypoalbuminemia. While nephrotic-range proteinuria in adults is characterized by protein excretion of 3.5 g or more per day, in children it is defined as protein excretion of more than 40 $mg/m^2/h$ or a first-morning urine protein/creatinine of 2-3 mg/mg creatinine or greater. In some embodiments, the nephrotic syndrome is pediatric nephrotic syndrome, which is the occurrence of pediatric nephrotic syndrome in a child.

In some embodiments, the method further includes administering an additional therapeutic agent for treating or preventing glomerular disease or chronic kidney disease. Preferably, the PPARγ agonist (e.g., GQ-16 or a GQ-16 derivative) is administered concomitantly with the additional therapeutic agent. Concomitantly, as used herein, means that the two drugs are administered either in combination or that the PPARγ agonist and the additional therapeutic agent are administered within a short period of time (e.g., a day or an hour) of each other such that their therapeutic effects overlap.

Therapeutic agents that are useful for treating chronic kidney disease include agents to manage blood pressure, blood sugar, and lower cholesterol. Management of blood sugar and lowering cholesterol are important because diabetes and heart disease are both cause and are exacerbated by chronic kidney disease. Angiotensin converting enzyme inhibitors or angiotensin II receptor antagonists are recommended as first-line agents since they have been found to slow the decline of kidney function.

Agents for treating glomerular disease include endothelin antagonists (Raina et al., Kidney Dis (Basel), 6(1):22-34 (2020)), agents that target the complement system (Andrighetto et al., Int J Mol Sci., 20(24) (2019)), and sodium-glucose co-transporter 2 (SGLT2) inhibitors (Davidson, J A, Postgrad Med., 131(4):251-260 (2019), the disclosures of which are incorporated herein by reference.

Glucocorticoids are the primary therapy for nephrotic syndrome, although they have serious side effects and are ineffective in ~20-50% of patients. However, a variety of non-steroid methods for treating nephrotic syndrome are also known. See Tune B. and Mendoa S., J Am Soc Nephrol., 8(5), 824-32 (1997), the disclosure of which is incorporated herein by reference. Non-steroidal immunosuppressants suitable for treatment of nephrotic syndrome include cytotoxic drugs such as cyclophosphamide and chlorambucil, calcineurin inhibitors such as cyclosporine and tacrolimus, inosine monophosphate dehydrogenase (IMPDH) inhibitors such as mycophenolate mofetil and mizoribine, and the anti-CD20 antibody rituximab.

Administration and Formulation

The pharmaceutical compositions used in the present invention comprise a PPARγ agonist, or pharmaceutically acceptable salts thereof, as the active ingredient. The pharmaceutical compositions may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The term "composition", as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

The PPARγ agonist(s) can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form, in which case solid pharmaceutical carriers are obviously employed. If desired, tablets may be coated by standard aqueous or non-aqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

The PPARγ agonist(s) may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethypiperideine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

The data obtained from the cell culture assays and animal studies can be used in formulating a range of dosage for use in humans. The dosage may vary depending upon the dosage form employed and the route of administration. A dose may be formulated in animal models to achieve a circulating plasma concentration range that includes the $IC_{50}$ (i.e., the concentration of the test compound which achieves a half-maximal inhibition of symptoms). Such information can be used to more accurately determine useful doses in humans. Levels in plasma may be measured, for example, by high performance liquid chromatography.

As defined herein, a therapeutically effective amount of the PPARγ agonist (i.e., an effective dosage) ranges from 0.001 to 40 mg/kg body weight, preferably 0.01 to 25 mg/kg body weight, more preferably 0.1 to 20 mg/kg body weight, and even more preferably 1 to 10 mg/kg, 2 to 9 mg/kg, 3 to 8 mg/kg, 4 to 7 mg/kg, or 5 to 6 mg/kg body weight. The active compounds can be administered once a day or one time per week for between 1 to 10 weeks, preferably between 2 to 8 weeks, more preferably between 3 to 7 weeks, and even more preferably for 4, 5, or 6 weeks. The skilled artisan will appreciate that certain factors may influence the dosage and timing required to effectively treat a mammal including, but not limited to, the severity of the disease or disorder, previous treatments, the general health and/or age of the mammal, and other diseases present. Moreover, treatment of a subject with a therapeutically effective amount of a PPARγ agonist can include a single treatment or, preferably, can include a series of treatments.

The present invention is illustrated by the following example. It is to be understood that the particular example, materials, amounts, and procedures are to be interpreted broadly in accordance with the scope and spirit of the invention as set forth herein.

EXAMPLE

Example 1: Selective Modulation of Nuclear Receptor PPARγ by a Partial Agonist Improves Glomerular Disease The inventors hypothesized that the downstream effects of PPARγ can be mechanistically dissociated and that selected manipulation of PPARγ by a novel partial agonist, GQ-16, will result in a better and targeted therapeutic advantage in glomerular disease. To test this hypothesis, we: 1) Determined and compared the ability of GQ-16 vs. Pio to provide reduction in proteinuria and glomerular injury, 2) Analyzed the systemic effects of complete vs. partial agonism of PPARγ, and 3) studied key molecular regulatory roles of PPARγ, in an animal model of glomerular disease.

Methods

Animal Studies: Glomerular Disease Model and Treatment with Pio and GQ-16

This study was approved by the Institution Animal Care and Use Committee at Nationwide Children's Hospital, and their guidelines were followed when performing the experiments. Male Wistar rats were intravenously (IV) injected with puromycin aminonucleoside (PAN) (Sigma-Aldrich, St. Louis, Mo.) (50 mg/kg) on Day 0, which induced proteinuria, while control rats were given IV injections of saline. The rats were treated by oral gavage with Pioglitazone (Alfa Aesar, Tewksbury, Mass.) (10 mg/kg), GQ-16 (40 mg/kg), or a sham vehicle daily. GQ-16 and Pio dosages were determined based on previous studies, and GQ-16 was synthesized as previously described. Amato et al., The Journal of biological chemistry, 287: 28169-28179 (2012). Spot urine and serum were collected, and body weights were recorded throughout the study. The rats were anesthetized with 3% isoflurane and sacrificed on Day 11, at which time blood was collected through the inferior vena cava with a 23-G needle into the 0.32% sodium citrate and 1.45 μM corn trypsin inhibitor, then processed to Platelet Poor Plasma (PPP) as described previously. Kerlin et al., Journal of the American Society of Nephrology: JASN, 26: 3009-3019 (2015). Kidneys were harvested, and the glomeruli were isolated using the sequential sieving method. Agrawal et al., Sci Rep, 6: 24392 (2016). Liver and white adipose tissue (WAT) epididymal fat were collected and flash frozen in liquid nitrogen.

Urinalysis

Urine was collected from rats daily throughout the study and resolved using sodium dodecyl sulfate-polyacrylamide gel electrophoresis (SDS-PAGE) on an 8% gel and stained with Coomassie Brilliant Blue G-250 (Alfa Aesar, Tewksbury, MA) to visualize the albumin bands. Urine protein: creatinine ratio (UPCr) analyses were performed on urine samples from Day 11 at the time of peak proteinuria by Antech Diagnostics GLP (Morrisville, N.C.) to quantify the proteinuria values.

Serum Chemistry

Serum albumin and cholesterol were measured using the ACE® albumin and cholesterol reagents (Alfa Wasserman Diagnostic Technologies, LLC, West Caldwell, NJ) on the Vet Axcel (Alfa Wasserman Diagnostic Technologies, LLC, West Caldwell, NJ) at the Clinical Pathology Services, The Ohio State University's College of Veterinary Medicine, according to the manufacturer's instructions.

Coagulopathy Measurement

Thrombin generation assays (TGA) were performed using the Technothrombin® TGA Kit (Technoclone, Vienna, Austria) and Reagent C (RC) Low on PPP samples collected from the rats to determine various parameters such as the endogenous thrombin potential (ETP) and peak thrombin concentration. These assays were performed at least in duplicate on various rat groups (n=4-7/group). Briefly, PPP at 1:1 ratio with buffer was added to black well plates, and RC Low added. Then TGA substrate was added just before reading on a Spectramax M2 Fluorescent Plate Reader (Molecular Devices, San Jose, CA).

RNA Isolation, Quantitative Real Time Reverse Transcription-Polymerase Chain Reaction Total RNA was extracted from isolated WAT epididymal fat and liver tissue samples using the RNeasy kit (Qiagen, Germantown, MD), following the manufacturer's instructions. Tissue samples in lysis buffer were placed in lock tubes with stainless-steel disruption beads and lysed at 30.0 Hz for 4 minutes using the Qiagen TissueLyser (Germantown, MD), followed by RNA isolation from the resulting lysate. Total RNA was isolated from glomeruli tissue samples using the mirVana™ Isolation Kit (Invitrogen, Carlsbad, CA), according to the manufacturer's instructions. Yield and purity were calculated for all isolated RNA samples by measuring the absorbance at 260, 280, and 230 nm and the ratios (both) with a spectrophotometer. 500 ng-1 μg of RNA was subjected to DNase (Invitrogen, Carlsbad, CA) digestion at room temperature for 15 minutes, which was then inactivated with 25 mM EDTA at 65° C. for 10 min. RNA was reverse transcribed using the iScript cDNA Synthesis Kit (Bio-Rad, Hercules, CA) according to the manufacturer's instructions. cDNA was used for quantitative reverse transcription-polymerase chain reaction (qRT-PCR) using gene specific and house-keeping primers. SYBR green (Bio-Rad, Hercules, Calif.) qRT-PCR was performed on the Applied Biosystems 7500 Real-Time PCR System. The PCR conditions were 95° C. for 10 minutes, 40× (95° C. for 15 seconds, 60° C. for 1 minute), followed by a melt curve to ensure specific products. The annealing temperature was at 60° C. for all genes except Pgc1a, Pparg, and Cd36 for which 52° C. annealing temperature was used. The melt curve conditions were 95° C. for 15 seconds, 60° C. for 1 minute, 30 seconds incremental increase to 95° C. and 60° C. for 15 seconds. The ΔΔCt method was used to analyze the results, including normalization to housekeeping genes (Rpl6 44 for glomeruli, Ppia 45, 46 for fat and liver). Pfaffl, M W, Nucleic acids research, 29: e45, 2001. Due to melt curve variation for Trpc6, amplified samples were also resolved on a 2% agarose gel, and densitometry was performed using ImageJ (National Institutes of Health, Bethesda, MD) software. Each gene was tested in triplicates for each tissue on at least three different rats per group.

Protein Isolation, SDS-PAGE and Western Blotting

To isolate protein from the glomeruli, liver, and fat tissues, the samples were lysed in a lock tube with RIPA buffer (1M Tris HCl, 0.5M EDTA, 5M NaCl, 10% SDS) containing protease inhibitor cocktail (Thermo Scientific, Waltham, MA) and phosphatase inhibitor cocktail (Alfa Aesar, Tewksbury, MA) and a stainless-steel disruption bead using a Qiagen TissueLyser (Germantown, Md.). Following lysis/homogenization at 30.0 Hz for 4 minutes (liver and fat) or 1 minute (glomeruli), samples were centrifuged for 10 minutes at 4° C. at 12,000 rpm. The supernatant was collected, and the proteins were resolved by SDS-PAGE and transferred to an Immobilon-P polyvinylidene difluoride (PVDF) Transfer Membrane (Millipore Sigma, St. Louis, MO). The membrane was blocked with 5% milk in phosphate buffer saline (PBS) with 0.1% Tween 20 (PBST) for 1 hour, followed by incubation with the primary antibody overnight [anti-Phospho-PPARγ-Ser 273 (Bioss, Woburn, MA), anti-PPARγ (Proteintech, Carlsbad, CA), and anti-GAPDH (Cell Signaling, Danvers, MA)]. The membrane was washed three times in PBST and incubated with the secondary antibody [anti-rabbit IgG (Jackson ImmunoResearch Laboratories, Inc, West Grove, PA)] in 5% milk in PBST for an hour. Protein bands were detected by chemiluminescence using the Chemidoc MP Imaging System (Bio-Rad, Hercules, CA). Densitometry was performed on the bands using ImageJ (National Institutes of Health, Bethesda, MD) software, and band density was subtracted from the background and normalized to GAPDH.

Statistical Analysis

Statistical analysis was performed using Mann-Whitney test, unpaired Student's t-test, and paired Student's t-test. Linear regression was used to quantify the correlation with proteinuria and other measurement values using the GraphPad Prism software version 8.2.0 for Windows (GraphPad Software, San Diego, CA). P value significance was depicted as: *$p<0.05$, $p<0.01$, *$p<0.001$, ****$p<0.0001$.

PPAR-Responsive Element Prediction

A PPARgene database was used to predict the sequence specific PPAR-responsive elements (PPRE) on all the target genes measured in this study. Fang et al., PPAR research, 2016: 6042162 (2016). Upon submitting the query, if the gene was predicted as a PPAR target gene, the query returned p-value and confidence level of the prediction and listed putative PPREs in the 5 kb transcription start site flanking region. Genes were assigned high-confidence category ($p>0.8$), medium-confidence category ($0.8\geq p>0.6$), and low-confidence category ($0.6\geq p>0.45$). Genes with p value ≤0.45 were predicted as negative.

Results

Figure 2A:
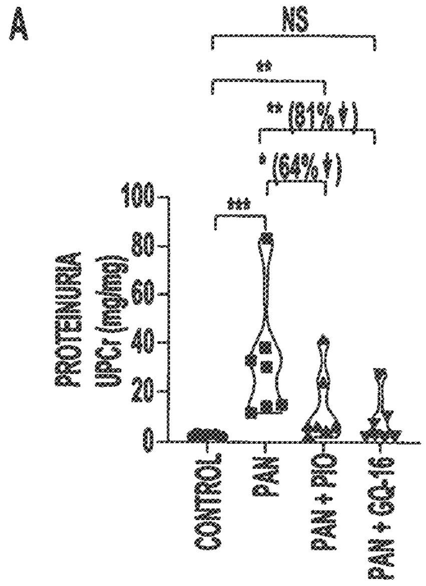
Figure 2B:
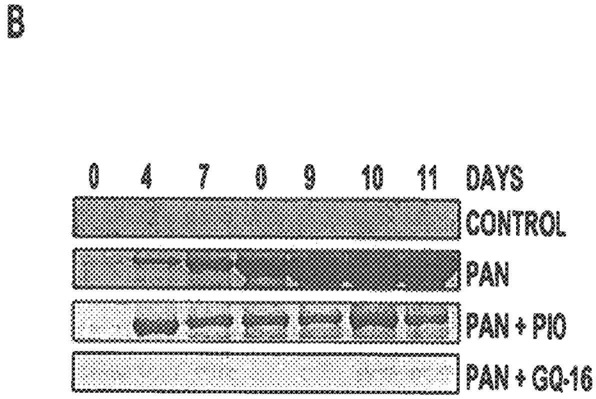

GQ-16 Reduces Proteinuria and Hypoalbuminemia with Increased Efficacy Compared to Pio in a Rat Model of PAN-Induced Nephropathy In order to assess the efficacy of GQ-16 and to compare it with a traditional agonist of PPARγ, Pio, in reducing proteinuria in a glomerular disease model, a PAN-induced nephropathy model was utilized. A single IV PAN injection of 50 mg/kg to male Wistar rats induced massive proteinuria on Day 11 (32.53±9.33 mg/mg; p=0.0006), which started appearing on Day 4 (FIGS. 2A and B). Control rats, which received IV saline injection, maintained baseline levels of urinary protein (2.28±0.25 mg/mg). Daily Pio treatment resulted in a significant mean reduction in PAN-induced proteinuria to 64% (13.17±5.51 mg/mg; p=0.05). Interestingly, GQ-16 treatment decreased PAN-induced proteinuria more robustly to 81% reduction (8.01±3.54 mg/mg; p=0.004) (FIGS. 2A and B). Additionally, the proteinuria levels with GQ-16 treatment were comparable to control levels (ns, p=0.07), while Pio treatment remained significantly different from Control (p=0.004).

Figure 2C:
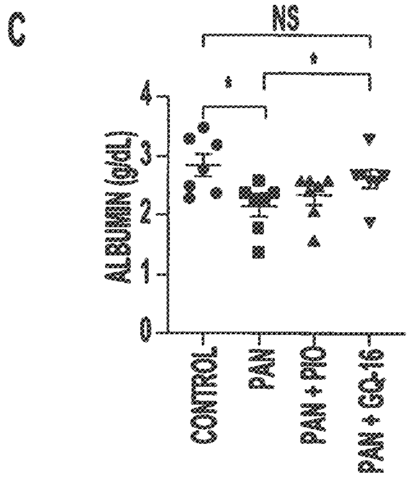
Figure 2D:
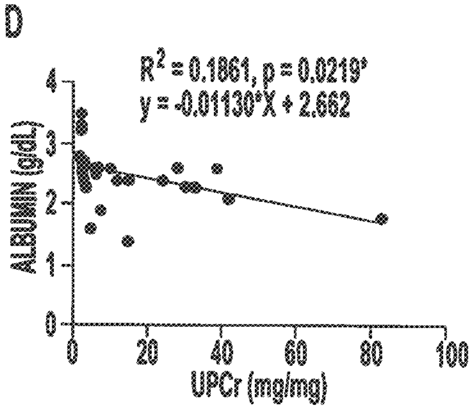

Assessment of serum albumin levels in these rats showed a decrease in PAN injected rats as compared to control rats (2.17±0.16 g/dL vs. 2.86±0.18 g/dL; p=0.02). Treatment with daily Pio resulted in a modest but insignificant increase in serum albumin (2.34±0.14 g/dL; p=0.26), while treatment with GQ-16 daily resulted in a significant increase in serum albumin levels (2.64±0.15 g/dL; p=0.014), which were comparable to control (p=0.63, ns) (FIG. 2C). Additionally, serum albumin showed a significant correlation to proteinuria in all the rats combined (p=0.02) (FIG. 2D).

Glomerular Gene Expression of Podocyte Marker Nphs1 and PPARγ Target Gene Nrf2 is Restored with Treatment with GQ-16

Figures 3A, 3B, 3C, 3D, 3E, 3F, 3G, 3H, 3I, 3J, 3K:
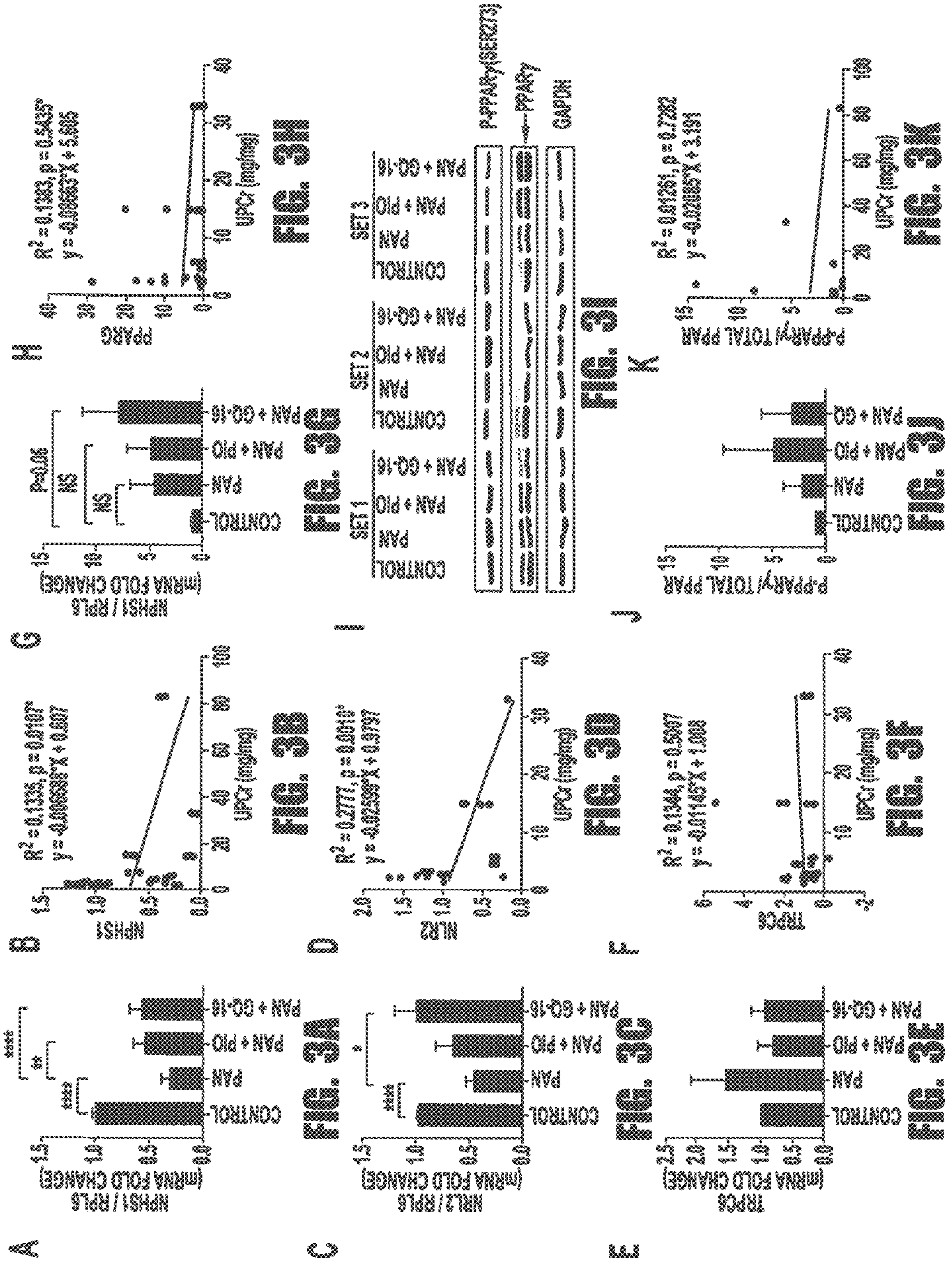

Since podocytopathy is a characteristic of proteinuria in glomerular disease and to understand the role of PPARγ activation in altering glomerular pathways, we measured the expression of relevant podocyte marker and genes in the glomeruli of nephrotic and treated rats. PAN-induced nephropathy resulted in reduction in the glomerular expression of podocyte marker Nphs1 (encoding for nephrin), a critical component of slit diaphragm, as well as Nrf2 (encoding for nuclear factor erythroid 2-related factor 2), a target gene downstream of PPARγ (FIG. 3A-D). Nphs1 expression was down-regulated with PAN and significantly restored with GQ-16 treatment and modestly with Pio treatment (FIG. 3A). Nphs1 expression also correlated with reduction in proteinuria in these rats (p=0.01) (FIG. 3B). Notably, while GQ-16 treatment resulted in marked restoration of Nrf2 expression as well, Pio treatment did not (FIG. 3C), and Nrf2 expression levels correlated strongly with reduction in proteinuria (p=0.001) (FIG. 3D). While Trpc6 showed a trend towards induction with PAN and reduction with both Pio and GQ-16 treatments, its correlation with proteinuria was not found to be significant (FIGS. 3E and F). Furthermore, we found that our gene expression data corroborated the prediction of PPREs on the target genes measured in this study using the 'PPARgene' database (Table 1). This database was developed using a machine learning method to predict novel PPAR target genes by integrating in silico PPRE analysis with high throughput gene expression data. For example, while both Nrf2 and Nphs1 are predicted to contain PPREs flanking their transcription start sites, Trpc6 did not show any predictive PPREs.

TABLE 1

PPAR-Responsive Element (PPRE) Prediction in Target Genes

| Gene | Tissue (Current Study) | p Value* | Confidence Level | PPREs Predicted[#] |
|---|---|---|---|---|
| Nrf2 | Glomerular | 0.45663 | low | 7 |
| Nphs1 | Glomerular | 0.63696 | medium | 4 |
| Trpc6 | Glomerular | — | — | — |
| Ap2/Fabp4 | WAT | 0.99997 | high | 10 |
| Cd36 | WAT | 0.97886 | high | 3 |
| Adipoq | WAT | 0.97153 | high | 12 |

TABLE 1-continued

PPAR-Responsive Element (PPRE) Prediction in Target Genes

| Gene | Tissue (Current Study) | p Value* | Confidence Level | PPREs Predicted[#] |
|------|------------------------|----------|------------------|----------------|
| Pparg | Glomerular/WAT | 0.91081 | high | 2 |
| Pgc1a | WAT | — | — | — |
| Adipsin | WAT | 0.96216 | high | 6 |
| Albumin | Hepatic | 0.63443 | medium | 2 |
| Abca1 | Hepatic | 0.99483 | high | 3 |
| Pcsk9 | Hepatic | — | — | — |
| F2 | Hepatic | 0.55991 | low | 4 |
| Serpinc1 | Hepatic | — | — | — |
| Ppia | Housekeeping (WAT, hepatic) | — | — | — |
| Rpl6 | Housekeeping (glomerular) | — | — | — |

Figure 4A:
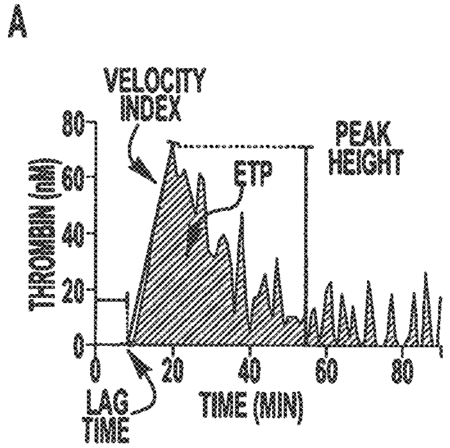
Figure 4B:
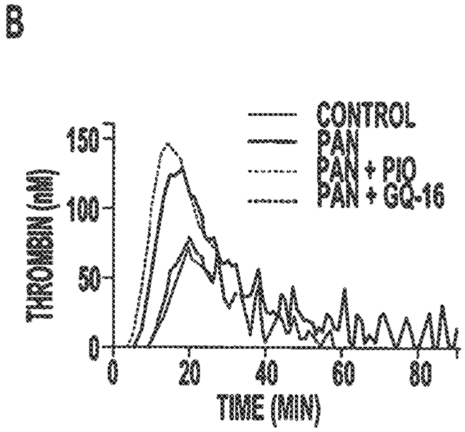
Figure 4C:
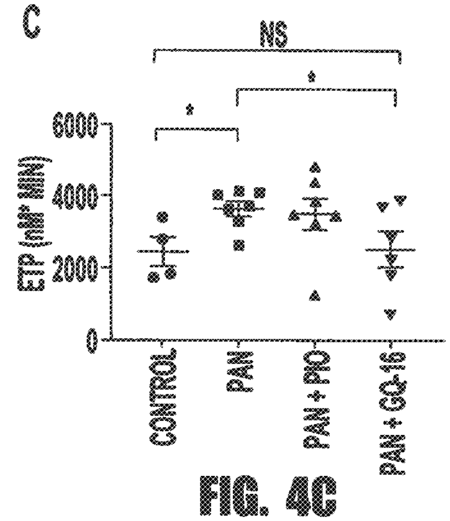
Figure 4D:
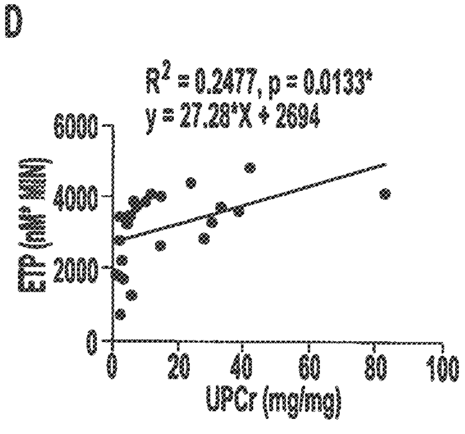

*Probability of being a PPAR target gene, higher value means a higher confidence
High-confidence (p > 0.8), median-confidence (0.8 ≥ p > 0.6), low-confidence category
(0.6 ≥ p > 0.45).
Genes with p value ≤ 0.45 were predicted as negative.
[#]Putative PPREs in the 5 Kb transcription start site (TSS) flanking region FIG. 4A and it is characterized by a short lag phase, area under the curve (or endogenous thrombin potential), peak thrombin, and velocity index. Representative curves from each of the study groups are shown in FIG. 4B. ETP is a consistently elevated thrombin generation parameter in NS, and we found it to be significantly increased in nephrotic rats (PAN, 3646±198.8 nM*min vs. Control, 2445±402.1 nM*min; p=0.014) (FIGS. 4B and C). This increase in ETP with PAN showed significant reduction with GQ-16 treatment (2544±489.0 nM*min; p=0.049), while Pio treatment did not have a detectable effect (3509±427.8 nM*min; p=0.77) (FIGS. 4B and C). Notably, ETP strongly correlated with proteinuria (p=0.01) in the nephrotic and treatment rats combined (FIG. 4D). In addition to ETP, other parameters such as peak thrombin generation, lag phase, and velocity index were also derived from these thrombin generation assays (Table 2). The time of the lag phase was significantly reduced with PAN compared to Control, and it showed a tendency to reverse back to increase lag phase with GQ-16 treatment (Table 2).

TABLE 2

Coagulation and Thrombin Generation Parameters

| Parameters | Control | PAN | PAN + Pio | PAN + GQ-16 | UPCr Correlation R ^ 2 | UPCr Correlation p value |
|------------|---------|-----|-----------|-------------|------------------------|--------------------------|
| ETP (nM*min) | 2445 ± 402.1 | 3646 ± 198.8* (p = 0.0143) | 3509 ± 427.8 | 2544 ± 489.0[#] (p = 0.0493) | 0.2477 | 0.0133[±] |
| Peak Thrombin (nM) | 98.97 ± 20.82 | 180.4 ± 27.02 (p = 0.0698) | 180.8 ± 29.50 | 134.0 ± 35.54 | 0.0282 | 0.4328 |
| Velocity Index (nM/min) | 16.08 ± 5.073 | 33.07 ± 8.570 | 34.67 ± 8.448 | 19.91 ± 6.643 | 0.0037 | 0.7775 |
| Lag Phase (min) | 10.38 ± 0.826 | 6.321 ± 0.713** (p = 0.006) | 7.714 ± 0.6974 | 9.250 ± 1.532 (p = 0.0956) | 0.2035 | 0.0269[±] |

*p < 0.05; **p < 0.01; compared to Control
[#]p < 0.05; compared to PAN
[±]p < 0.05; correlation Next, we determined the ability of Pio and GQ-16 to alter Pparg gene expression and its phosphorylation status at Serine 273 position. Phosphorylation of PPARγ at Ser273 has been shown to be an important determinant of its activity for its insulin sensitizing effects 30 (Hall et al., Cell metabolism, 32: 665-675 e666 (2020)), and thus to understand its role in the reduction of proteinuria, we measured it's levels in the glomeruli of nephrotic and Pio and GQ-16-treated rats. While Pparg expression tended to be greater in PAN and PAN+Pio groups compared to control, and somewhat increased with GQ-16 treatment, it was not significant (p=0.06) (FIG. 3G). Additionally, the overall expression in all the rats did not correlate with proteinuria (FIG. 3H). Furthermore, the phosphorylation status of PPARγ at Ser273 position seemed to be unaltered with Pio and GQ-16 in PAN-nephrotic rats (FIGS. 3I and J), and it did not correlate with proteinuria (FIG. 3K).

Figure 5A:
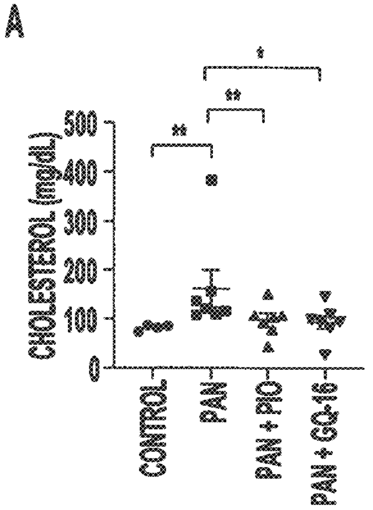
Figure 5B:
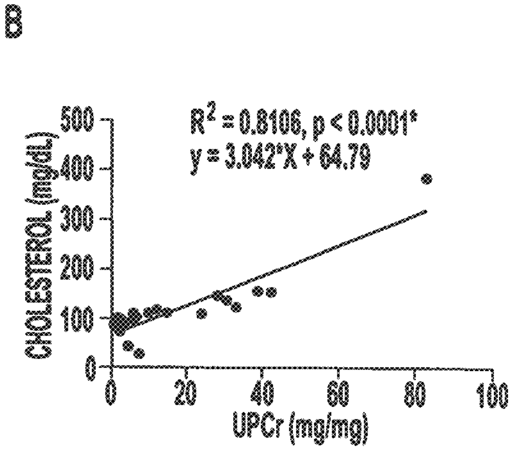
Figure 5C:
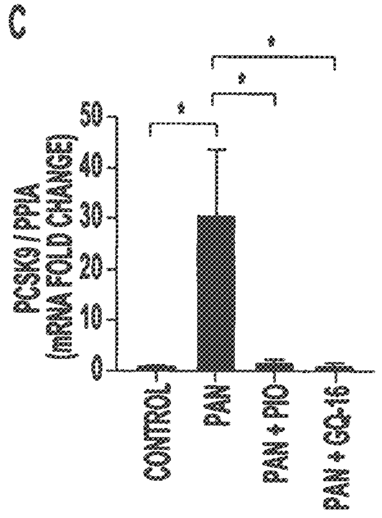
Figure 5D:
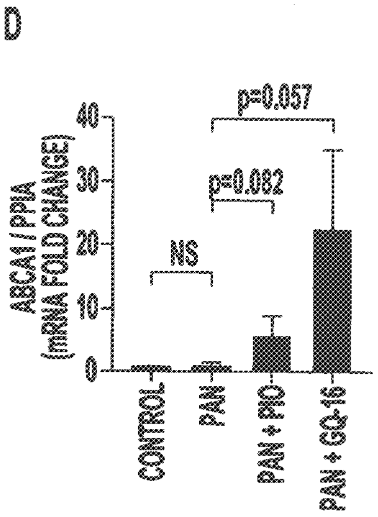

Glomerular Disease Associated Hypercoagulopathy is Corrected with GQ-16 Treatment We have previously shown a significant correlation between hypercoagulopathy and proteinuria during NS, and correction of hypercoagulopathy with glucocorticoid treatment, which is a standard treatment for NS. Waller et al., Physiol Rep, 8: e14515, 2020. We thus measured thrombin generation parameters in our model of NS, their alteration with treatment with Pio and GQ-16, and correlation with proteinuria. A typical thrombin generation curve is shown in GQ-16 Treatment Reduces Glomerular Disease-Associated Hypercholesterolemia and Alters the Hepatic Gene Expression Dyslipidemia is a major feature of NS and glomerular disease 8, manifesting as hypercholesterolemia. In order to understand the role of PPARγ agonists in altering dyslipidemia and the expression of genes involved in lipid metabolism, we measured total cholesterol levels in the serum and the expression of relevant genes in the liver of nephrotic and treated rats. PAN-induced nephropathy resulted in significant increase in total cholesterol levels compared to control (PAN, 161.6±37.58 mg/dL vs. Control, 81.75±2.72; p=0.006) (FIG. 5A). Both GQ-16 and Pio treatments resulted in significant mean reduction of PAN-induced hypercholesterolemia to 86% (93.14±13.36 mg/dL; p=0.019) and 80% (97.86±12.37 mg/dL; p=0.01), respectively. Moreover, serum cholesterol levels strongly correlated with proteinuria (P<0.0001) in the nephrotic and treatment rats combined (FIG. 5B). Pcsk9 (encoding for proprotein convertase subtilisin/kexin type 9) expression in the liver tissue was significantly upregulated with PAN-induced nephropathy (~30 fold) and restored to control levels with both GQ-16 and Pio treatments (FIG. 5C). While Abca1 (encoding for ATP binding cassette subfamily A member 1) expression was unchanged with PAN, it showed a trend in increased expression with treatments (~23 fold with GQ-16 treatment, p=0.057) (FIG. 5D).

As liver is also the major source of albumin (Alb) and coagulation proteins, such as prothrombin (F2) and anti-thrombin (SerpinC1), and we have observed hypoalbuminemia and hypercoagulopathy with PAN injury and their respective corrections with GQ-16, we measured the hepatic gene expression in the nephrotic and treatment rats. While Alb was not induced with PAN, both F2 and SerpinC1 showed a tendency to be induced with PAN and reduced with GQ-16 ($p=0.07$).

Figure 6A:
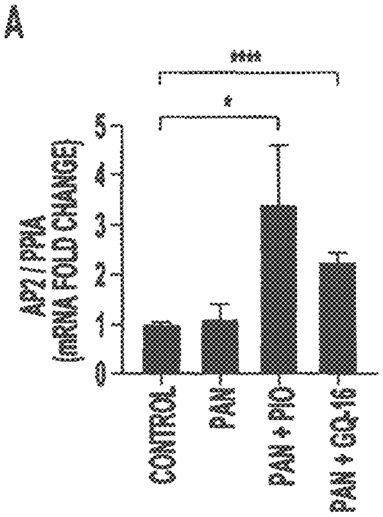
Figure 6B:
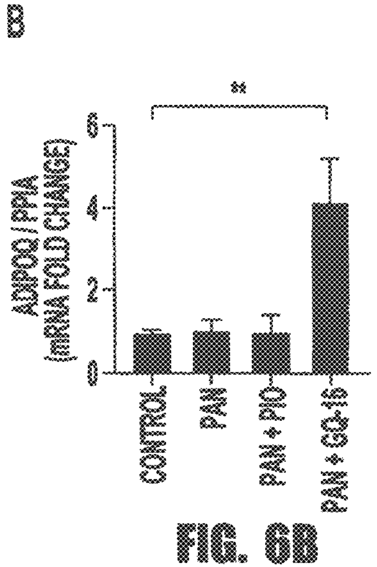
Figure 6C:
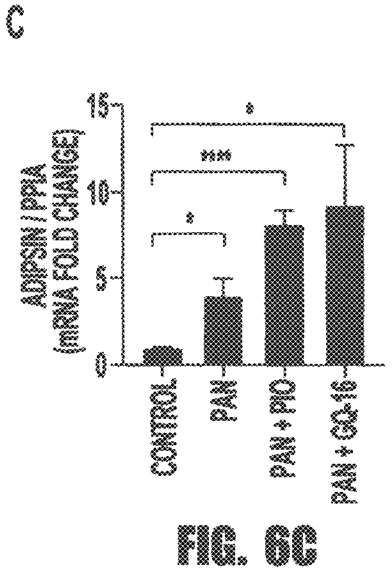
Figure 6D:
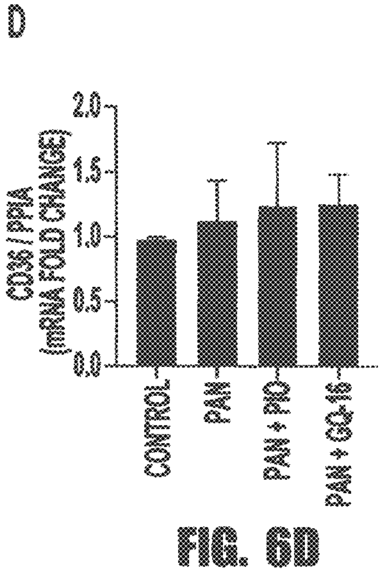

GQ-16 and Pio Treatments Distinctly Alter the Gene Expression of Adipogenic Pathways in the White Adipose Tissue Adipogenic pathways are typically induced with PPARγ activation and we thus measured alterations in the expression of genes involved in these pathways in the epididymal fat of WAT with Pio and GQ-16 treatments. While the expression of Ap2 (Fabp4, encoding for fatty acid binding protein 4), which causes weight gain, was more pronounced with Pio (~3.4 fold) as compared to GQ-16 (~2.2 fold) (FIG. 6A), expression of insulin sensitizing or secreting adipokines, Adipoq (adiponectin) and Adipisn (Cfd, complement factor D) was induced more robustly with GQ-16 as compared to Pio (FIGS. 6B and C). Although a trend was observed towards an increase in Cd36 (fatty acid transporter) expression, with both Pio and GQ-16, no significant differences were observed (FIG. 6D). Notably, as opposed to the studies involving PPARγ in the context of diabetes and obesity, it is not possible to study the direct effect of weight gain in the current study as PAN-induced treatment itself leads to a modest reduction in weight gain in these rats. Nevertheless, we observed that while the weight reduction in nephrotic rats was maintained with GQ-16 treatment, Pio treatment did not show any significant difference from control rats.

GQ-16 Treatment Induces Pparg Expression and Reduces a Exon-5 Splice Variant Form While PPARγ co-activator 1α (Pgc1α) showed a trend in increase with Pio and GQ-16 treatments (FIG. 7A), both of these treatments induced the expression of Pparg (FIG. 7B), which seemed to be more prominent in WAT than in the glomeruli (FIG. 7B and FIG. 3G). Additionally, recently a naturally spliced variant form of Pparg has been identified in human adipocyte progenitor cells and in WAT of obese and diabetic patients. Aprile et al., Cell reports, 25: 1577-1592 e1576 (2018). We were able to detect the expression of a Δ exon 5 splice variant form of Pparg, which was found to be decreased with injury as well as with both Pio and GQ-16 treatments in the WAT when normalized to the total Pparg expression (FIG. 7C). Notably GQ-16 further reduced the levels of Δexon 5 Pparg variant.

Discussion

Glomerular disease is the leading cause of ESKD in the United States, and NS, characterized by high-grade proteinuria, is one of the most common forms of glomerular disease. Furthermore, NS is typically associated with hypoalbuminemia, hypercholesterolemia, systemic immune dysregulation, hypercoagulopathy, and edema. Glucocorticoids are the standard treatment for NS, but have a lot of side effects, and 10-50% of adult and pediatric NS patients can be resistant to steroid treatment. Thus, there is an urgent and critical need to develop new alternative therapies for NS and glomerular disease with increased efficacy and reduced side effects. In order to do so, we and others have previously reported that PPARγ agonists not only provide beneficial protective effects in type II diabetes and DN, but also in various models of non-diabetic glomerular disease. Yang et al., Journal of the American Society of Nephrology: JASN, 20: 2380-2388, (2009). However, targeting PPARγ via widely marketed anti-diabetic drugs or traditional TZDs has been re-evaluated due to significant side effects such as weight gain, heart failure, bone fracture and bladder cancer 32-37. In the current study we hypothesized that the downstream effects of PPARγ can be mechanistically dissociated and that selected manipulation of PPARγ by a novel partial agonist, GQ-16, will result in a better and targeted therapeutic advantage in glomerular disease. Our results revealed that GQ-16 is more efficacious than Pio in reducing proteinuria in a PAN-induced animal model of glomerular disease or NS (FIG. 8). Our results further demonstrated that while both GQ-16 and Pio restored glomerular Nphs1 and hepatic Pcsk9 expression and reduced hypercholesterolemia, the beneficial effects of GQ-16 were also associated with restoration of glomerular Nrf2, and reduction in disease associated hypoalbuminemia and hypercoagulopathy. Furthermore, in WAT, GQ-16 treatment resulted in decreased weight-gain associated induction of Ap2 (fatty acid binding protein), increased expression of insulin sensitizing adipokines, and decreased expression of Δexon5 splice variant, as compared to Pio treatment. These findings together indicate that PPARγ can be selectively molecularly modulated by its partial agonist GQ-16, in order to enhance the beneficial proteinuria reducing effects and reduce the glomerular disease associated-features, as well as side-effects conferred by traditional PPARγ full agonists.

PPARγ is attributed to the therapeutic basis of TZDs to treat diabetes, since it improves insulin sensitivity and decreases insulin demands. Yki-Jarvinen, H, The New England journal of medicine, 351: 1106-1118 (2004). While PPARγ is the master regulator of glucose and lipid metabolism and regulator of adipogenesis, in the last couple of decades, various preclinical studies and meta-analyses have highlighted its direct beneficial role in kidney cells in addition to its favorable systemic effects in the context of diabetes. Tanimoto et al., Metabolism, 53: 1473-1479 (2004). Notably, in the last decade, we and others have documented the beneficial roles of TZDs in directly protecting podocytes from injury (Agrawal et al., Nat Rev Nephrol, 14, 57-70 (2018)), in reducing proteinuria and glomerular injury in various animal models of glomerular disease such as minimal change disease, focal segmental glomerulosclerosis (FSGS), and crescentic glomerulonephritis and even in improving clinical outcomes in NS patients refractory to steroid treatment. More recently, breakthrough discoveries in the field of PPARγ biology suggest that the beneficial insulin-sensitizing activities of PPARγ can be dissociated from its harmful adipogenic activities. While the beneficial activities have been linked with inhibition of obesity-linked phosphorylation at Ser 273, the harmful adipogenic and osteoclastic effects are linked with its agonistic effects of traditional full agonists. Choi et al., Nature, 466: 451-456 (2010). This has led to the development of mechanistically distinct novel compounds, including GQ-16, that have weak traditional PPARγ agonistic activity (adipogenic) and associated weight gain effects, but very good anti-diabetic activity. Amato, et al., The Journal of biological chemistry, 287: 28169-28179 (2012).

In this example, we have specifically demonstrated that GQ-16 reduces proteinuria in a rat model of NS with better efficacy than Pio. This 84% reduction in proteinuria by GQ-16 was found to be comparable to controls as well as to the previously described reduction with high dose glucocorticoids (79%). GQ-16 treatment was also more effective than Pio in correcting another characteristic feature of NS, hypoalbuminemia in PAN NS. Furthermore, podocyte injury and loss are characteristic features of proteinuria in NS and the integrity of podocyte signaling pathways and slit diaphragm is paramount to their proper structure and function. Nephrin is a critical podocyte marker and an essential component of the slit diaphragm, which is either mutated in the congenital form of NS (Finnish Type) or decreased in expression in various forms of glomerular disease. Grahammer et al., Nat Rev Nephrol, 9: 587-598 (2013). In accordance with its important role in glomerular function, we found that Nphs1 expression correlated with proteinuria and it was significantly reduced in the glomeruli of the nephrotic rats and increased with treatments with PPARγ agonists. NRF2 is the master regulator of oxidation pathways and is well known to have cytoprotective and anti-inflammatory effects. Tonelli et al., Antioxid Redox Signal, 29: 1727-1745, 2018. It also plays a critical role in regulating PPARγ expression and its complete deletion has been recently demonstrated to result in decreased podocyte PPARγ and aggravated course of glomerular disease as reported in a rapid proliferative glomerulonephritis model. Moreover, enhanced podocyte injury seen in the animal models of glomerular disease with podocyte specific Pparg deletion is also associated with reduced expression and activity of NRF2. Accordingly, we found a significant decrease in the expression of glomerular Nrf2 in nephrotic rats, which was only mildly restored with Pio, but completely by GQ-16 to control levels. These results suggest that GQ-16 may be superior to Pio in reducing glomerular injury and in restoring the PPARγ downstream pathways.

Furthermore, PPARγ has been shown to be phosphorylated in obesity models at the Ser273 site and dephosphorylated with the insulin sensitizing effects of PPARγ agonists. Moreover, in an in vitro assay, GQ-16 has been shown to dephosphorylate PPARγ like traditional TZDs. Interestingly, our results demonstrate that relative phosphorylated PPARγ levels (at Ser273) remain unaltered with PAN injury and subsequent Pio and GQ-16 treatments. This result suggests that while PPARγ-Ser273 is known to play a major role in determining the insulin sensitizing effects of PPARγ in the adipose tissue, the same mechanism may not play a role in determining its proteinuria-reducing effects in the glomeruli.

Our previous observations have found increased ETP to be very well-correlated with increased proteinuria during NS and its decrease with standard treatment in both human studies and in animal models. In the current study, we find a good correlation of ETP with proteinuria, significant increase with injury, and a decrease with GQ-16 treatment. Our previous study demonstrated that Pio treatment decreased ETP in concert with proteinuria during PAN NS. However, Pio significantly increased ETP when given to healthy control rats, suggesting its inherent role in increasing ETP 42. In the current study, we failed to observe a significant reduction in ETP with Pio in NS, which could be because of Pio's inherent ability to increase ETP. Additionally, Pio used in the present study was from a different manufacturer, and the time between the last Pio dose and PPP collection was decreased by approximately 8 hours. This likely contributed to increased levels of Pio in the blood at the time of ETP measurement, as the systemic pharmacokinetic profile of Pio suggests that it peaks at 1.5-2 hours and its half-life is approximately 8-9 hours. Hanefeld, M, Int J Clin Pract Suppl: 19-25 (2001). Overall, our studies suggest that partial agonism of PPARγ provides a better correction of hypercoagulopathy, than full agonism by Pio.

Dysregulated lipid metabolism is one of the other major features of NS and glomerular disease. Hepatic levels of PCSK9 are known to be upregulated in glomerular disease which contributes to dyslipidemia by degrading the low-density lipoprotein (LDL) receptor and decreased LDL uptake by the liver. Inhibition of PCSK9 using anti-PCSK9 monoclonal antibodies and siRNAs has gained high clinical importance due to its lipid-lowering effects in the conditions of hypercholesterolemia and is gaining traction in the context of NS with the emergence of case reports and new clinical trials. Our results corroborate the importance of PCSK9, as we found a significant induction in its gene expression in the liver of nephrotic rats. Moreover, both Pio and GQ-16 robustly and significantly reduced the PAN-induced hepatic Pcsk9 expression to control levels. ABCA1 plays an important role in cholesterol efflux and experimental evidence in animal models of FSGS suggests that increase in ABCA1 activity mainly in liver and other peripheral organs, including in podocytes, is associated with improved proteinuria. Vaziri, N D, Nat Rev Nephrol, 12: 37-47, 2016. Interestingly, while the increase was not significant, we observed a trend in its increase with Pio and to a larger extent with GQ-16 treatments, in our animal model of NS.

GQ-16 has been shown to exhibit modest adipogenic activity as compared to TZDs as shown by reduced transactivation activity and aP2 induction. Coelho et al., PloS one, 11: e0154310, (2016). Findings in obese Swiss male mice indicated that in addition to exhibiting insulin-sensitizing properties, 14-day treatment with GQ-16 induced decreased edema, weight gain, and visceral WAT mass in response to high fat diet, despite increasing energy consumption 39, 40. These effects were accompanied by induction of thermogenesis-related genes in epididymal fat depots, suggesting that browning of visceral WAT may have contributed to weight loss. These results strongly support that PPARγ activation by partial agonists, devoid of full agonism-related unfavorable effects, may be a strategy to induce browning of WAT and hence to treat obesity and diabetes. Specifically, our current study supports this theory in the context of non-diabetic disease. Our studies show that while both Pio and GQ-16 induce Ap2 expression, it is more robustly induced by Pio as compared to GQ-16. Furthermore, both full and partial PPARγ agonists are known to increase the expression of insulin sensitizing adipokines, adiponectin and adipsin, as well as the fatty acid transporter CD36 38. While we did not observe a significant change in the expression levels of CD36, both Pio and to a larger extent GQ-16, induced Adipsin and ADIPOQ expression. Overall, the results suggest that GQ-16 has a better adipogenic profile than Pio in a rat model of NS treatment.

PPARγ exists in mainly two major isoforms, γ1 and γ2, which are a result of different promoter usage as well as alternative splicing (FIG. 1). Fajas et al., The Journal of biological chemistry, 272: 18779-18789 (1997). While γ1 is ubiquitously expressed, including in podocytes, γ2 is mostly restricted to adipose tissue and liver. Moreover, the recently identified Δ exon-5 splice variant form of Pparg has been shown to function as a dominant negative form of by reducing the adipogenic potential of precursor cells and its increased expression in the adipose tissue has shown positive correlation with body mass index in obese and diabetic patients. We have observed the presence of a Δ exon5 spliced form of Pparg in the WAT, which was reduced with PAN injury and further decreased with GQ-16 treatment. Although speculative, it is possible that a decrease in Δexon5 Pparg with PAN injury could be an adaptive mechanism, and its further reduction by GQ-16 in our study serves as a positive feedback loop to enhance PPARγ activity.

In summary, our studies indicate that selective modulation of PPARγ by a partial agonist is more efficacious than a full PPARγ agonist in reducing proteinuria, hypoalbuminemia and hypercoagulopathy and in decreasing drug-associated side effects in a PAN-induced animal model of glomerular disease. These findings not only deepen our molecular understanding of the role of PPARγ in glomerular disease and provide future clinical implications for partial agonists such as GQ-16 as a potential promising treatment modality for NS, but also lend the possibility of its potential benefits in diabetic nephropathy.

The complete disclosure of all patents, patent applications, and publications, and electronically available materials cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A method of treating or reducing the risk that a subject will develop or chronic kidney disease, comprising administering to the subject a therapeutically effective amount of PPARγ agonist, or a pharmaceutically acceptable salt thereof.

2. The method of claim 1, wherein the PPARγ agonist is a GQ-16 derivative.

3. The method of claim 1, wherein the PPARγ agonist is selected from the group consisting of GQ-16, MRL-24, and PA-082.

4. The method of claim 1, wherein the PPARγ agonist is GQ-16.

5. The method of claim 1, wherein treatment decreases proteinuria in the subject.

6. The method of claim 1, wherein treatment decreases hypercoagulopathy in the subject.

7. The method of claim 1, wherein the subject is human.

8. The method of claim 1, wherein the method is used to reduce the risk that a subject will develop chronic kidney disease.

9. The method of claim 1, wherein the method is used to treat chronic kidney disease in a subject having been diagnosed with chronic kidney disease.

10. The method of claim 1, wherein the method further comprises administering an additional therapeutic agent comprising an ACE inhibitor or antidiabetic agent for treating or reducing the risk that a subject will develop chronic kidney disease.

11. The method of claim 1, wherein the PPARγ agonist is administered together with a pharmaceutically acceptable carrier.

* * * * *